United States Patent [19]

Campbell et al.

[11] Patent Number: 5,990,112

[45] Date of Patent: *Nov. 23, 1999

[54] INHIBITORS OF METALLOPROTEASES PHARMACEUTICAL COMPOSITIONS COMPRISING SAME AND METHODS OF THEIR USE

[75] Inventors: David Campbell, San Mateo; Gary C. Look; Anna Katrin Szardenings, both of Santa Clara; Dinesh V. Patel, Fremont, all of Calif.

[73] Assignee: Affymax Technologies N.V., Greenford, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/670,713

[22] Filed: Jun. 18, 1996

[51] Int. Cl.$^6$ ........................ A61K 31/495; C07D 241/08
[52] U.S. Cl. .......................... 514/255; 544/385; 544/231; 544/349; 544/350; 514/249
[58] Field of Search .............................. 544/385; 514/255

[56] References Cited

U.S. PATENT DOCUMENTS

| | | | |
|---|---|---|---|
| 4,609,667 | 9/1986 | Clark et al. | 514/367 |
| 4,940,709 | 7/1990 | Shimazaki et al. | 514/253 |
| 5,728,830 | 3/1998 | Kanda et al. | 544/5 |
| 5,736,539 | 4/1998 | Graham et al. | 514/218 |
| 5,817,751 | 10/1998 | Szardenings et al. | 530/317 |

FOREIGN PATENT DOCUMENTS

| | | |
|---|---|---|
| 0 181 152 | 5/1986 | European Pat. Off. . |
| 96/00391 | 1/1996 | WIPO . |

OTHER PUBLICATIONS

Bernstein, et al., "Preparation of a Diketopiperazine Analog of Leukotriene $D_4$ ($LTD_4$)", Tetrahedron Letters, vol. 26, No. 16, pp. 1951–1954, 1985.

Dudman, et al., "Homocysteine Thiolactone and Experimental Homocysteinemia", Biochemical Medicine, (27), pp. 244–253 (1982).

Rossbach, et al., Abstract, for Physiol. –Chem. Inst., University Tuebingen, Tuebingen, Germany, Z. Naturforsch. B (1971), 26(11), pp. 1144–1151.

Schneider, et al., "Kinetik der Reaktion von Imidazol–SH- –Verbindungen mit N–Athyl–maleinimid", Hoppe–Seyler's Z. Physiol. Chem., pp. 1521–1530, Dec. 1969.

Richter, et al., "Penicillamine: An Extractable Chiral Auxiliary Providing Excellent Stereocontrol", Tetrahedron: Asymmetry, vol. 7, No. 2, pp. 427–434 (1996).

Chemical Abstracts, vol. 117, No. 33, 1992, Abstract No. 0275b, Nachev: Synthesis of N–Polyfunctional Substituted L–Phenylalanine, p. 849, col. 1, XP002040920.

Birkedal–Hansen et al, *Critical Reviews in Oral Biology and Medicine*, 4 (2), pp. 197–250 (1993).

Vincenti et al, *Arthritis & Rheumatism*, 37, p. 1115–1126 (1994).

Beyermann et al, *J. Org. Chem.* 55, p. 721–728 (1990).

*Primary Examiner*—Emily Bernhardt
*Attorney, Agent, or Firm*—Gerald F. Swiss; Lauren L. Stevens

[57] ABSTRACT

Novel inhibitors of metalloproteases are disclosed. Such compounds are useful in pharmaceutical compositions and methods for treating or controlling disease states or conditions which involve tissue breakdown, such as rheumatoid arthritis.

5 Claims, No Drawings

INHIBITORS OF METALLOPROTEASES PHARMACEUTICAL COMPOSITIONS COMPRISING SAME AND METHODS OF THEIR USE

BACKGROUND OF THE INVENTION

1. Field of the Invention

This invention relates to novel pharmaceutically active compounds which are inhibitors of metalloproteases. Pharmaceutical compositions comprising these compounds as well as methods of their use for treating or controlling disease states or conditions associated with such enzymes are also described.

2. State of the Art

Metalloproteases are involved in a large number of disease states and other conditions in human and other animals. The metalloproteases are a family of enzymes containing zinc at the active site, which facilitates the catalytic hydrolysis of various protein substrates. A subfamily of the metalloprotease family is known as the matrix metalloproteases because these enzymes are capable of degrading the major components of articular cartilage and basement membranes. The matrix metalloproteases include stromelysin, collagenase, matrilysin and gelatinase, among others.

Stromelysin (aka. proteoglycanase, matrix metalloproteinase-3, MMP-3, procollagenase activator, "transin"), collagenase (aka. interstitial collagenase, matrix metalloproinase-1, MMP-1, type II collagenase), and gelatinase (aka. type IV collagenase, matrix metalloproteinase-2, MMP-2, 72 kDa-gelatinase or type V collagenase, matrix metalloproteinase-9, MMP-9, 95 kDa-gelatinase) are metalloendoproteinases secreted by fibroblasts and chondrocytes, and are capable of degrading the major connective tissue components of articular cartilage or basement membranes. Human rheumatoid synovial collagenase is approximately 50% identical to human stromelysin (Whitham et al., *Biochem. J.*, 240:913–916 (1986)). Gelatinase (MR ~72,000) has been isolated from rheumatoid fibroblasts (Okada et al., *Eur. J. Biochem.*, 194:721–730 (1990)). A higher molecular weight gelatinase (MR ~95,000; aka. type-V collagenase, matrix metalloproteinase-9, MMP-9) is also secreted by fibroblasts and monocytes and may be involved in cartilage degradation.

Metalloproteases are apparently involved in several arthritis conditions, including osteoarthritis (OA) and rheumatoid arthritis (RA). These diseases are largely due to the loss of articular cartilage. Elevated levels of stromelysin and collagenase have been detected in joints of arthritic humans and animals (Hasty et al., *Arthr. Rheum.*, 33:388–397 (1990); Krane et al., In *The Control of Tissue Damage*, A. B. Glauert (ed.), Elsevier Sci. Publ., Amsterdam, 1988, Ch. 14, pp. 179–195; Blanckaert et al., *Clin. Chim. Acta*, 185:73–80 (1989)). Each enzyme is secreted from these cells as an inactive proenzyme which is subsequently activated. There is evidence that stromelysin may be the in vivo activator for collagenase and gelatinase, implying a cascade for degradative enzyme activity (Fo et al., *Arch. Biochem. Biophys.*, 267:211–216 (1988); Murphy et al., *Biochem. J.*, 248:265–268 (1987); Ogata et al., *J. Biol. Chem.*, 267:3581–3584 (1992)). The synthesis of the gelatinase proenzyme is not coordinately regulated with the other two metalloproteinases. The role of gelatinase in the tissue destruction of articular cartilage appears different from the other two enzymes.

Stromelysin and collagenase are also implicated in the articular cartilage damage associated with septic arthritis. Bacterial infections of the joints can elicit an inflammatory response that may then be perpetuated beyond what is needed for removal of the infective agent, resulting in permanent damage to structural components. Bacterial agents have been used in animal models to elicit an arthritic response with the appearance of proteolytic activities (Case et al., *J. Clin Invest.*, 84:1731–1740 (1989); Williams et al., *Arthr. Rheum.*, 33:533–541 (1990)).

Secreted proteinases such as stromelysin, collagenase, and gelatinase play an important role in processes involved in the movement of cells during metastatic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis.

Periodontal diseases such as gingivitis are also characterized by metalloprotease expression. Both collagenase and stromelysin activities have been isolated from fibroblasts isolated from inflamed gingiva (Uitto et al., *J. Periodontal Res.*, 16:417–424 (1981)). Enzyme levels have been correlated to the severity of gum disease (Overall et al., *J. Periodontal Res.*, 22:81–88 (1987)).

Stromelysin has been implicated in the degradation of structural components of the glomerular basement membrane (GBM) of the kidney, the major function of which is to restrict passage of plasma proteins into the urine (Baricos et al., *Biochem. J.*, 254:609–612 (1988)). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases.

Metalloproteases may also be involved in the rupturing of atherosclerotic plaques leading to coronary thrombosis. The tearing or rupturing of atherosclerotic plaques is the most common event initiating coronary thrombosis. Destabilization and degradation of the connection tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin messenger RNA have been found to be localized to individual cells in atherosclerotic plaques removed from heart transplant patients at the time of surgery (Henney et al., *Proc. Natl. Acad. Sci. USA*, 88:8154–8158 (1991)).

Degenerative aortic disease associated with thinning of the medial aortic wall is another condition in which matrix metalloproteases may play a role. Aneurysms are often associated with atherosclerosis in this tissue. Increased levels of the matrix metalloproteinases have been identified in patients with aortic aneurysms and aortic stenosis (Vine et al., *Clin. Sci.*, 81:233–239 (1991)).

Expression of metalloproteinases, including stromelysin and collagenase, is observed in unfertilized eggs and zygotes and at further cleavage stages and increased at the blastocyst stage of fetal development and with endoderm differentiation (Brenner et al., *Genes & Develop.*, 3:848–859 (1989)). By analogy to tumor invasion, a blastocyst may express metalloproteinases in order to penetrate the extracellular matrix of the uterine wall during implantation. In addition, evidence exists that collagenase is important in ovulation processes. Collagenase apparently facilitates penetration of a covering of collagen over the apical region of the follicle, allowing the ovum to escape. There may also be a role for strome-lysin activity during ovulation (Too et al., *Endocrin.* 115:1043–1050 (1984)).

Proteolytic processes have also been observed in the ulceration of the cornea following alkali burns (Brown et al., *Arch. Ophthalmol.*, 81:370–373 (1969)). Collagenolytic and stromelysin activity have also been observed in dystrophobic epidermolysis bullosa (Kronberger et al., *J. Invest. Dermatol.*, 79:208–211 (1982); Sawamura et al., *Biochem. Biophys. Res. Commun.*, 174:1003–1008 (1991)).

In addition to degrading structural components of the extracellular matrix, stromelysin can degrade other in vivo substrates, including the $\alpha_1$-proteinase inhibitor, and may therefore influence the activities of other proteinases such as elastase (Winyard et al., *FEBS Lett.*, 279(1):91–94 (1991)).

Because metalloproteases play a role in so many diseases and other conditions, inhibitors of these enzymes have been studied as possible therapeutic agents. In vitro experiments measuring the effect of matrix metalloendoproteinase inhibitors on proteoglycan release from rabbit cartilage explants suggest that stromelysin inhibition may be effective in preventing articular cartilage degradation (Caputo et al., *J. Orthopedic Res.*, 6:103–108 (1988)). Evidence also suggests that inhibitors of stromelysin, collagenase, and gelatinase will be useful to control tumor metastasis (Matrisian et al., *Proc. Natl. Acad. Sci. USA*, 83:9413–9417 (1986); Wilhelm et al., *Proc. Natl. Acad. Sci. USA*, 84:6725–6729 (1987); Liotta, et al., *Lab. Invest.*, 49:636–649 (1983); Reich et al., "Inhibitors of collagenase IV and cell adhesion reduce the invasive activity of malignant tumor cells", in *Metastasis: Ciba Foundation Symposium*; Wiley, Chichester, 1988, pp. 193–210). An inhibitor of collagenase has been shown to be effective in preventing ovulation (Woessner et al., *Steroids*, 54:491–499 (1989)). Mercapto-containing peptides inhibit the collagenase isolated from alkali-burned rabbit cornea (Burns et al., *Invest. Ophthalmol.*, 30:1569–1575 (1989)).

Thiol carboxylic acid derivatives that inhibit collagenase are disclosed in U.S. Pat. Nos. 5,109,000; 4,595,700; 4,371, 466. Additional collagenase inhibitor compounds are disclosed in European Patent Application Publication Nos. 0 423 943; 0 273 689; 0 322 184; and 0 185 380, and in International Patent Application Publication Nos. WO 88/06890 and WO 94/07481.

Collagenase inhibitors have also been designed around the cleavage site of the a-chain sequence of Type II collagen (Johnson et al., *J. Enzym. Inhib.*, 2:1–22 (1987)). One such inhibitor, N-[3-(benzyloxy-carbonyl)amino-1-carboxy-n-propyl]-L-leucyl-O-methyl-L-tyrosine, N-methylamide, prepared at G. D. Searle, Inc., is a potent inhibitor of human rheumatoid synovial collagenase ($IC_{50}$=0–8 $\mu$M). This compound also inhibits rabbit bone proteoglycanase ($IC_{50}$=0.5 $\mu$M) (Delaisse et al., *Biochem. Biophys. Res. Commun.*, 133:483–90 (1985)).

However, significant obstacles continue to stand in the way of clinical exploitation of metalloprotease inhibitors. First, there is very little to guide one in developing a specific inhibitor for each enzyme. In preliminary studies of rabbit proteoglycanase with substrates and inhibitors, little was found to indicate the enzyme's requirements for hydrolysis or inhibition beyond a preference for hydrophobic residues at the $P_1'$ position (Shaw et al., *Adv. Inflam. Res.*, 12: 67–79 (1988)). More extensive studies with a series of substrates revealed that stromelysin will tolerate nearly every amino acid residue around the scissile bond (Fields et al., unpublished results presented at the Matrix Metalloproteinase Conference, September 1989, Sandestin, Fla.).

Toxicity is a second obstacle to therapeutic use of previously known metalloprotease inhibitors. For example, certain hydroxamic acids have been suggested as collagenase inhibitors as in U.S. Pat. No. 4,599,361 and European Patent Application Publication No. 0 236 872. U.S. Pat. Nos. 5,304,604, 5,240,958 and 5,310,763 also disclose hydroxamic acid derivatives which act as inhibitors of metalloproteases involved in tissue degradation, such as collagenase, stromelysin (proteoglycanase), gelatinase and collagenase (IV).

Although these hydroxamic acid compounds are effective inhibitors of matrix metalloproteases, the hydroxamic acid moiety is potentially toxic. See, for example, Musser et al., *J. Med. Chem.*, 29:1429–1435 (1986); Baililien et al., *Am. J. Vet. Res.*, 74:2604–2611 (1986); Rodman et al., *R.L. Clin. Pharmacol. Ther.*, 42:346–350 (1987); Williams et al., *N. Engl. J. Med.*, 311:760–764 (1984); Yoshioka et al., *Mutat. Res.*, 170:93–102 (1986); Gillissen et al., *Carcinogenesis*, 15:39–45 (1994); Gillissen et al., *Carcinogenesis*, 13:1699–1703 (1992); Fishbein et al., *Science*, 142:1069–1070 (1963);and Borenfreund et al, *J. Nat. Cancer Inst*, 32:667–679 (1964). As a result, there are few, if any, hydroxamic acid based drugs in use.

The wide spectrum of clinical indications for matrix metalloprotease inhibitors establishes a clear need for matrix metalloprotease inhibitors that have satisfactory inhibition activity. It is not a simple matter, however, to predict what variations in known compounds would retain or even increase activity. The present invention fulfills this need for novel effective metalloprotease inhibitors.

SUMMARY OF THE INVENTION

The invention provides novel matrix metalloprotease inhibitors that are highly active. In one aspect, the present invention relates to a compound of formula:

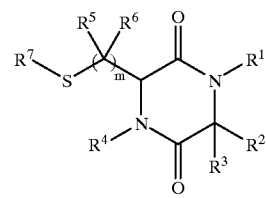

wherein $R^1$ and $R^4$ are independently selected from the group consisting of hydrogen and —$CH_2R^8$ and —$CHR^8R^9$;

$R^2$, $R^3$, $R^5$, $R^6$ and $R^8$ are independently selected from the group consisting of
(i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and X is selected from the group consisting of a bond, O, and NR' where R' is as defined above;

(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and Y is selected from the group consisting of a bond and NR' where R' is as defined above;

(v) alkenyl groups of from 2 to 10 carbon atoms;

(vi) alkynyl groups of from 3 to 10 carbon atoms;

(vii) carboxyl groups;

(viii) carboxyl ester groups wherein the ester group comprises from 1 to 12 carbon atoms;

(ix) heterocycles, either saturated, unsaturated, or aromatic, having from 2 to 6 carbon atoms and 1 to 3 ring hetero atoms selected from the group consisting of nitrogen, oxygen and sulfur, optionally substituted;

(x) R—C(O)— groups where R is hydrogen or an alkyl group of from 1 to 12 carbon atoms, optionally substituted on the alkyl group;

(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$; and (xii) arylalkyl, optionally substituted on either the aryl group and/or the alkyl group; or wherein $R^2$, $R^3$ and the carbon to which they are attached form a cycloalkyl or heterocyclic group; or $R^1$ and $R^2$ and the carbon and nitrogen to which they are attached, respectively, form a heterocyclic group; or $R^4$ and $R^5$ and the carbon and nitrogen to which they are attached, respectively form a heterocyclic group;

$R^7$ is selected from the group consisting of hydrogen and alkyl of from 1 to 12 carbon atoms, $R^8C(O)$— and $R^8S$— where $R^8$ is as defined above;

$R^9$ is hydrogen, alkyl, substituted alkyl, aryl, substituted aryl, heterocyclic or substituted heterocyclic; and n is an integer from 1 to 3.

Preferably, $R^4$, $R^5$ and $R^6$ are independently selected from the group consisting of hydrogen and lower alkyl.

Preferably, $R^1$ and $R^2$ are independently alkyl groups (including cycloalkyl), which may be optionally substituted.

In one preferred embodiment, $R^4$ is hydrogen and $R^1$ is —$CHR^8R^9$ where $R^8$ is an amido group such as —NR'C(O)R" and —$C(O)NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is —$C(O)NH_rR'_s$ where R' is alkyl, including cycloalkyl, substituted alkyl, aryl, substituted aryl, heterocyclic and substituted heterocyclic.

In another preferred embodiment, $R^1$ is hydrogen and $R^4$ is —$CHR^8R^9$ where $R^8$ is an amido group such as —NR'C(O)R" and —$C(O)NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is —$C(O)NH_rR'_s$ where R' is alkyl, including cycloalkyl, substituted alkyl, aryl, substituted aryl, heterocyclic and substituted heterocyclic.

In still another preferred embodiment, $R^2$ includes alkaryl and substituted alkaryl groups including —$CH_2$—$C_6H_4Z$ where Z is hydroxy, alkyl, substituted alkyl, alkoxy, substituted alkoxy, amido, amino, aryloxy, carboxyl, halo, mercapto, cyano, nitro, —$SO_3$, —$SO_2NH_2$ at any location on the phenyl (—$C_6H_4$ ring).

Even more preferably, $R^1$ is cyclohexyl and $R_2$ is methylcyclohexyl. Particularly preferred compounds include the compounds recited in Table I below including all isomers thereof (e.g., R and S stereo isomers, cis and trans positional isomers, etc.) In Table I, n is 1 and $R^3$, $R^4$, $R^5$, $R^6$ and $R^7$ are hydrogen.

TABLE I

| $R^1$ | $R^2$ | No. |
|---|---|---|
| cyclohexyl-$CH_2$— | cyclohexyl-$CH_2$— | 1 |
| (p-methoxy-φ)$CH_2$— | cyclohexyl-$CH_2$— | 2 |
| (2-quinolinyl)-$CH_2$— | cyclohexyl-$CH_2$— | 3 |
| (2-quinolinyl)-$CH_2$— | (p-nitro-φ)$CH_2$— | 4 |
| (p-methoxy-φ)$CH_2$— | (p-nitro-φ)$CH_2$— | 5 |
| $CH_3(CH_2)_2$— | (p-nitro-φ)$CH_2$— | 6 |
| cyclohexyl-$CH_2$— | $CH_3(CH_2)_2$— | 7 |
| (p-methoxy-φ)$CH_2$— | φ-$CH_2$— | 8 |
| (p-methoxy-φ)$CH_2$— | 3-($C_5H_4N$)$CH_2$— | 9 |
| (p-methoxy-φ)$CH_2$— | 4-($C_5H_4N$)$CH_2$— | 10 |
| (p-methoxy-φ)$CH_2$— | (m-nitro-φ)$CH_2$— | 11 |
| (p-methoxy-φ)$CH_2$— | (o-nitro-φ)$CH_2$— | 12 |
| (p-methoxy-φ)$CH_2$— | (p-cyano-φ)$CH_2$— | 13 |
| (p-methoxy-φ)$CH_2$— | (p-C(O)$NH_2$-φ)$CH_2$— | 14 |
| (p-methoxy-φ)$CH_2$— | (p-C(O)OH-φ)$CH_2$— | 15 |
| (p-methoxy-φ)$CH_2$— | (p-$NH_2$-φ)$CH_2$— | 16 |
| (p-methoxy-φ)$CH_2$— | (p-NHC(O)$CH_3$-φ)$CH_2$— | 17 |
| (p-methoxy-φ)$CH_2$— | (p-$SO_3$H-φ)$CH_2$— | 18 |
| (p-methoxy-φ)$CH_2$— | (p-$SO_2NH_2$-φ)$CH_2$— | 19 |
| (p-methoxy-φ)$CH_2$— | (p-$OCF_3$-φ)$CH_2$— | 20 |
| (p-methoxy-φ)$CH_2$— | —(p-$CF_3$-φ)$CH_2$— | 21 |
| —CH—C(O)NH-cyclohexyl<br>    \|<br>    $CH_2CH_3$ | —(p-nitro-φ)$CH_2$— | 22 |
| —CH—C(O)NH-cyclohexyl<br>    \|<br>    $CH_2CH_3$ | —(p-$CF_3$-φ)$CH_2$— | 23 |

Also provided are pharmaceutical compositions that include these metalloprotease inhibitor compounds in an amount effective for treating or controlling disease states associated with metalloproteases in patients in need of such treatment and a pharmaceutically acceptable carrier with the proviso that these metalloproteases do not include collagenase-1 or stromelysin-1. Methods for treating or controlling disease states or conditions involving tissue breakdown or inflammatory conditions are also provided. These methods involve administering to a patient in need of such treatment an effective amount of a metalloprotease inhibitor compound, generally as a pharmaceutical composition. Such disease states involve, for example, arthritic diseases such as rheumatoid arthritis and osteoarthritis, septic arthritis, articular cartilage degradation, Reiter's syndrome, pseudogout, juvenile rheumatoid arthritis, scleroderma, soft tissue rheumatism, polychodritis and tendinitis for bone resorption diseases such as osteoporosis, Paget's disease, hyperparathyroidism and cholesteatoma; for the recessive classes of dystrophic epidermolysis bullosa where the disease is linked to the overproduction of metalloprotease-1; for periodontal disease and related consequences of gingival collagenase production of PMNL collagenase-1 production following cellular infiltration to inflamed gingiva; for ulceration including corneal, epidermal, or gastric ulceration and more specifically, for corneal ulceration induced by alkali or other burns, by radiation, by vitamin deficiency or retinoid deficiency; for degenerative aortic disease associated with thinning of the media aortic wall and thus the prevention of events leading to acute and often times fatal aortic aneurysms; for use as a birth control agent and for preventing ovulation; for glomerular disease (e.g., proteinuria), coronary thrombosis (e.g., atherosclerotic plagues), Crohn's disease, multiple sclerosis and the cachexia associated with cancer or human immunodeficiency virus infection; and optionally in combination with current chemotherapy and/or radiation, for systemic chemotherapy of cancer, as well as the promotion of wound healing.

A further aspect of the present invention is a method of inhibiting mammalian metalloproteases in mammals afflicted with a disease state in which the metalloprotease has a role in the etiology of the disease such as those listed above. As before, such mammalian metalloproteases do not include collagenase-1 or stromelysin-1.

DETAILED DESCRIPTION OF THE INVENTION

I. Terminology

"Collagenase-1" refers to mammalian instititial collagenase-1 also known in the art as MMP-1. While other collagenases are known, they are not included in this definition of collagenase-1.

"Stromelysin-1" refers to the specific matrix metalloprotease identified in the art as stromelysin-1 which is sometimes referred to as MMP-3.

"Alkyl" refers to a cyclic, branched, or straight chain alkyl group containing only carbon and hydrogen, preferably having from 1 to 12 carbon atoms. This term is further exemplified by groups such as methyl, heptyl, —(CH$_2$)$_2$—, —(CH$_2$)$_q$—, —(CH$_2$)$_q$, —(C$_6$H$_{11}$), wherein q is from 1 to 5, adamantyl, and the like.

"Substituted alkyl" refers to a cyclic, branched, or straight chain alkyl group of from 1 to 12 carbon atoms having from 1 to 3 substituents selected from the group consisting of halogen, alkoxy, substituted alkoxy, thioalkoxy, substituted thioalkoxy (optionally wherein the sulfur atom of the thioalkoxy or substituted thioalkoxy group is oxidized to the sulfinyl or sulfonyl derivative), acyl, acyloxy, amido, amino, N-alkylamino, N,N-dialkylamino, aminotosyl, t-butoxycarbonylamino, hydroxyl, mercapto, carboxy, carboxyalkyl, carboxamide, benzyloxy, heterocyclic, aryl, heteroaryl, and substituted aryl and substituted heterocyclic. The particular substituents for the substituent alkyl groups are selected to be "non-interfering" so as not to eliminate or severely decrease the metalloprotease inhibition activity of the compound.

"Alkoxy" refers to —O-alkyl and includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to —O-substituted alkyl and includes, by way of example, —OCF$_3$, —OCH$_2$—φ and the like.

"Amide" or "amido" refers to the groups —NR'C(O)R" and —C(O)NH$_r$R'$_s$ where R' and R" are independently selected from hydrogen, alkyl, aryl, arylalkyl, or heteroaryl and where r=0–2, s=0–2 and r+s=2 (including substituted alkyl, substituted aryl, substituted arylalkyl and substituted heteroaryl).

"Amino" refers to the group —NR'R", where R' and R" are independently hydrogen, alkyl, substituted alkyl, aryl or substituted aryl.

"Amino acid" refers to any of the naturally occurring amino acids, as well as synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al (1977) *Review of Physiological Chemistry*, 16th Ed., Lange Medical Publications, pp. 21–24. One of skill in the art will appreciate that the term "amino acid" also includes β-, γ-, δ-, and ω-amino acids, and the like. Unnatural amino acids are also known in the art, as set forth in, for example, Williams (ed.), *Synthesis of Optically Active α-Amino Acids*, Pergamon Press (1989); Evans et al., *J. Amer. Chem. Soc.*, 112:4011–4030 (1990); Pu et al., *J. Amer. Chem. Soc.*, 56:1280–1283 (1991); Williams et al., *J. Amer. Chem. Soc.*, 113:9276–9286 (1991); and all references cited therein.

As used herein, the twenty conventional amino acids and their abbreviations follow conventional usage (see IMMUNOLOGY-A SYNTHESIS, 2nd Edition, E. S. Golub and D. R. Gren, Eds., Sinauer Associates, Sunderland, Mass. (1991), which is incorporated herein by reference). Amino acid residues are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Stereoisomers (e.g., D-amino acids) of the twenty conventional amino acids, unnatural amino acids such as α,α-disubstituted amino acids, N-alkyl amino acids, and other unconventional amino acids may also be suitable components for compounds of the present invention. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

"Aryl" or "Ar" refers to an unsaturated aromatic carbocyclic group of from 6 to 14 carbon atoms having a single ring (e.g., phenyl) or multiple condensed rings (e.g., naphthyl or anthryl) carbon atoms, which can optionally be unsubstituted or substituted with from 1 to 3 substituents selected from hydroxy, alkyl, substituted alkyl, alkoxy, substituted alkoxy, amido, amino, aryloxy, carboxyl, halo, mercapto, cyano, nitro, —SO$_3$, —SO$_2$NH$_2$ and other non-interfering substituents. Preferred aryls include phenyl and alkyl substituted phenyl.

"Arylalkyl" refers to the groups —R—Ar and —R—HetAr, where Ar is an aryl group (including substituted aryl groups), HetAr is a heteroaryl group (including substituted heteroaryl groups) and R is a straight-chain or branched-chain alkyl group or substituted alkyl group. Examples of arylalkyl groups include benzyl, —CH$_2$CH$_2$φ, and furfuryl. Benzyl is preferred.

"Carboxy" or "carboxylic acid" refers to the group —COOH.

"Ester" or "carboxyl ester" refers to the group —C(O)OR where R is alkyl, aryl, arylalkyl, or heteroaryl (including substituted alkyl, substituted aryl, substituted heteroaryl, or substituted arylalkyl).

"Halo" or "halogen" refers to fluoro, chloro, bromo and iodo and preferably is either chloro or bromo.

"Heterocycle" or "heterocyclic" refers to a monovalent saturated, unsaturated or aromatic (heteroaryl) carbocyclic group having a single ring or multiple condensed rings having at least one hetero atom, such as nitrogen, sulfur or oxygen within the ring, which can optionally be unsubstituted or substituted with from 1 to 3 substituents selected from the group consisting of hydroxy, alkyl, substituted alkyl, alkoxy, substituted alkoxy, aryl, substituted aryl, halo, mercapto, and other non-interfering substituents. Preferably, heterocycles are from 1 to 12 carbon atoms and from 1 to 4 hetero atoms.

"Heteroaryl" or "HetAr" refers to a monovalent aromatic heterocyclic group having a single ring (e.g., pyridyl or furyl) or multiple condensed rings (e.g., indolizinyl or benzo[b]thienyl). Preferably, the heteroaryl has from 2 to 12 carbon atoms and 1 to 4 heteroatoms selected from oxygen, nitrogen and sulfur within the ring which can optionally be substituted with from 1 to 3 substituents selected from the group consisting of hydroxy, alkyl, substituted alkyl, alkoxy, substituted alkoxy, aryl, substituted aryl, halo, mercapto, and other non-interfering substituents.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline. Preferred heteroaryls include pyrrole and pyridine.

"Hydroxy" or "hydroxyl" refers to the group —OH.

"Mercapto", "sulphydryl", or "thiol" refers to the group —SH.

"Protecting group" refers to a chemical group which generally exhibits the following characteristics: 1) the group must react selectively with the desired functionality in good yield to give a derivative that is stable to future projected reactions; 2) the protecting group must be selectively removable from the protected substrate to yield the desired functionality; and 3) the protecting group must be removable in good yield by reagents that do not attack one or more of the other functional group(s) generated or present in the projected reaction(s). Examples of protecting groups can be found in Greene et al. (1991) *Protective Groups in Organic Synthesis*, 2nd Ed. (John Wiley & Sons, Inc., New York).

Sidechain protecting groups may be used for certain amino acid derivatives having reactive functionalities, such as hydroxyl, carboxyl, amino, mercapto, guanidino, imidazolyl, indolyl and the like. The particular protecting groups used for any functional group requiring protection are generally known in the art. Exemplary sidechain protecting groups are acetyl, benzoyl, benzyl, t-butyl, and the like for hydroxyl; cyclohexyl, benzyl, methyl, ethyl, t-butyl, and the like for carboxyl; benzyl, 4-methylbenzyl, 4-methoxybenzyl, acetyl, acetamidomethyl, trephenylmethyl (trityl) and the like for mercapto; t-butyoxycarbonyl (Boc), benzyloxycarbonyl (Cbz), 9-fluroenylmethoxycarbonyl (Fmoc), phthaloyl (Pht), P-toluenesulfonyl (Tos), trifluoroacetyl, 2-(trimethylsilyl)-ethoxycarbonyl (TEOC), and the like for amino; 2,4-dinitrophenyl, benzyloxymethyl, Tos, Boc, Trityl, and the like for imidazolyl; formyl, Cbz, TEOC, 2,2,2-trichloroethyl carvamate (TROC), and the like for indolyl; and tosyl, nitro, bis(l-adamantyloxycarbonyl) and the like for guanidino.

Functional group protecting groups may be removed, if desired, by treatment with one or more deprotecting agents in an inert solvent of solvent mixture. For examples of protecting groups and suitable deprotecting agents, see Bodansky, M. and Bodansky, A., *The Practice of Peptide Synthesis*, Springer-Verlag, Inc. (1984); and Greene, T. W. and Wuts, P., *Protective Groups in Organic Synthesis* (2d ed.), John Wiley & Sons, Inc. (1991).

"Substituted" as applied to any moiety preferably means substituted with one or more (typically up to five) substituents selected from the group consisting of:

alkoxy of from 1 to 12 carbon atoms in an alkyl group,
alkenyl groups of from 2 to 10 carbon atoms,
alkynyl groups of from 3 to 10 carbon atoms,
hydroxyl,
halo,
cycloalkyl of from 3 to 8 carbon atoms,
cyano,
nitro,
amino,
mono- and di-alkylamines of from 1 to 12 carbon atoms in each alkyl group,
—SH,
—SR where R is an alkyl group of from 1 to 12 carbon atoms,
carboxyl,
carboxyl esters of from 1 to 12 carbon atoms in the ester moiety,
—NR'C(O)—X—R" where R' and R" are independently selected from the group consisting of hydrogen and alkyl of from 1 to 12 carbon atoms, aryl or heteroaryl groups optionally substituted with from 1 to 3 substituents on the aryl or heteroaryl moiety selected from the group consisting of halo, hydroxyl, amino, cyano, carboxyl, nitro, alkyl of from 1 to 12 carbon atoms, and alkoxy of from 1 to 12 carbon atoms (preferred aryl groups have from 6 to 10 carbon atoms and preferred heteroaryl groups have from 2 to 9 carbon atoms and from 1 to 3 ring hetero atoms selected from the group consisting of nitrogen, oxygen and sulfur and X is selected from the group consisting of a bond, O and NR' where R' is as defined above.

II. The Compounds The present invention provides compounds of the following formula:

Formula I

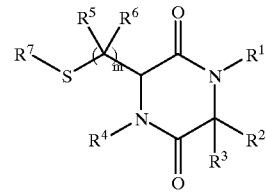

wherein $R_1$ and $R^4$ are independently selected from the group consisting of hydrogen and —$CH_2R^8$ and —$CHR^8R^9$;

$R^2, R^3, R^5, R^6$ and $R^8$ are independently selected from the group consisting of (i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and X is selected from the group consisting of a bond, O, and NR' where R' is as defined above;
(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and Y is selected from the group consisting of a bond and NR' where R' is as defined above;
(v) alkenyl groups of from 2 to 10 carbon atoms;
(vi) alkynyl groups of from 3 to 10 carbon atoms;
(vii) carboxyl groups;
(viii) carboxyl ester groups wherein the ester group comprises from 1 to 12 carbon atoms;
(ix) heterocycles, either saturated, unsaturated, or aromatic, having from 2 to 6 carbon atoms and 1 to 3 ring hetero atoms selected from the group consisting of nitrogen, oxygen and sulfur, optionally substituted;
(x) R—C(O)— groups where R is hydrogen or an alkyl group of from 1 to 12 carbon atoms, optionally substituted on the alkyl group;
(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$; and
(xii) arylalkyl, optionally substituted on either the aryl group and/or the alkyl group; or wherein $R^2$, $R^3$ and the carbon to which they are attached form a cycloalkyl or heterocyclic group; or $R^1$ and $R^2$ and the carbon and nitrogen to which they are attached, respectively, form a heterocyclic group; or $R^4$ and $R^5$ and the carbon and nitrogen to which they are attached, respectively form a heterocyclic group;

$R^7$ is selected from the group consisting of hydrogen and alkyl of from 1 to 12 carbon atoms, $R^8C(O)$— and $R^8S$— where $R^8$ is as defined above;

$R^9$ is hydrogen, alkyl, substituted alkyl, aryl, substituted aryl, heterocyclic or substituted heterocyclic; and n is an integer from 1 to 3.

Preferably, $R^4$, $R^5$ and $R^6$ are independently selected from the group consisting of hydrogen and lower alkyl.

Preferably, $R^1$ and $R^2$ are independently alkyl groups (including cycloalkyl), which may be optionally substituted.

In one preferred embodiment, $R^4$ is hydrogen and $R^1$ is —$CHR^8R^9$ where $R^8$ is an amido group such as —NR'C(O)R" and —C(O)$NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is —C(O)$NH_rR'_s$ where R' is alkyl, including cycloalkyl, substituted alkyl, aryl, substituted aryl, heterocyclic and substituted heterocyclic.

In another preferred embodiment, $R^1$ is hydrogen and $R^4$ is —$CHR^8R^9$ where $R^8$ is an amido group such as —NR'C(O)R" and —C(O)$NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is —C(O)$NH_rR'_s$ where R' is alkyl, including cycloalkyl, substituted alkyl, aryl, substituted aryl, heterocyclic and substituted heterocyclic.

In still another preferred embodiment, $R^2$ includes alkaryl and substituted alkaryl groups including —$CH_2$—$C_6H_4Z$ where Z is hydroxy, alkyl, substituted alkyl, alkoxy, substituted alkoxy, amido, amino, aryloxy, carboxyl, halo, mercapto, cyano, nitro, —$SO_3$, —$SO_2NH_2$ at any location on the phenyl (—$C_6H_4$ ring).

Even more preferably, $R^1$ is cyclohexyl and $R_2$ is methylcyclohexyl. Particularly preferred compounds include the compounds recited in Table I above.

As used herein, compounds of the present invention include derivatives of the above compound of Formula I, having any substitutions which do not eliminate or significantly reduce their ability to bind metalloproteases. For example, as previously stated, the compounds of the present invention are optionally substituted with a functional group. Any art-recognized functional group which does not eliminate or significantly reduce the compound's ability to bind metalloproteases are contemplated, including, but not limited to ester, amide acid, amine, alcohol, ether, and thioether, etc. Symmetrical and asymmetrical disulfides are also specifically included in the compounds of the present invention.

In addition, compounds of this invention can, depending on the nature of the functional groups, form addition salts with various inorganic and organic acids and bases. Pharmaceutical salts of the compounds of the present invention suitable for administration by a variety of routes are known in the art and need not be described herein in detail. Pharmaceutically acceptable salts include, but are not limited to, salts of (1) organic carboxylic acids such as acetic acid, propionic acid, glycolic acid, pyruvic acid, oxalic acid, malic acid, malonic acid, succinic acid, maleic acid, fumaric acid, tartaric acid, citric acid, cinnamic acid, mandelic acid, salicylic acid, benzoic acid, lactic, tartaric, isothionic, lactobionic and succinic acids; organic sulfonic acids such as methanesulfonic, ethanesulfonic, benzenesulfonic and p-toluylsulfonic acids; (2) inorganic acids such as hydrogen halide acids (e.t., hydrochloric acid and hydrobromic acid), sulfuric acid, nitric acid, and phosphoric acid; (3) alkali metals such as lithium, sodium and potassium. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium), ammonium, and $NW_xH_y$ bases and salts wherein each of x and y are 0 to 4 and x+y is 4, and wherein W is a ($C_1$–$C_{18}$) alkyl. Salts can also be formed from a carboxylic acid and an organic base, such as trimethylamine, diethylamine, ethanolamine, piperidine, isopropylamine, choline, caffeine, and the like.

Solvates, e.g., hydrates, of the compounds of the present invention are also included within the scope of the present invention. Methods of solvation to produce such solvates are generally known in the art.

The present invention also includes prodrugs of the compounds of Formula I. Various forms of prodrugs are well known in the art, for example, as discussed in Bundgaard (ed.), *Design of Prodrugs*, Elsevier (1985); Widder et al. (ed.), *Methods in Enzymology*, vol. 42, Academic Press, 309–396 (1985); Krogsgaard-Larsen et al. (ed.), "Design and Application of Prodrugs", *Textbook of Drug Design and Development*, Chapter 5, 113–191 (1991); Bundgaard, *Advanced Drug Delivery Reviews*, 8:1–38 (1992); Bundgaard et al., *Journal of Pharmaceutical Sciences*, 77:285 (1988); and Kakeya et al., *Chem. Pharm. Bull.*, 32:692 (1984).

There are several chiral centers in the compounds of the present invention because of the presence of asymmetric carbon atoms. The presence of several asymmetric carbon atoms gives rise to a number of diastereomers with the appropriate R or S stereochemistry at each chiral center. Compounds of Formula I and, where appropriate, all other formulae in this specification, including the claims, are to be understood to include all such individual stereoisomers and mixtures (for example, racemic mixtures) thereof.

II. Preparation

Compounds of the present invention can be readily prepared by either solution phase or solid phase synthetic techniques. For example, a preferred solution phase synthesis is outlined in the following reaction scheme:

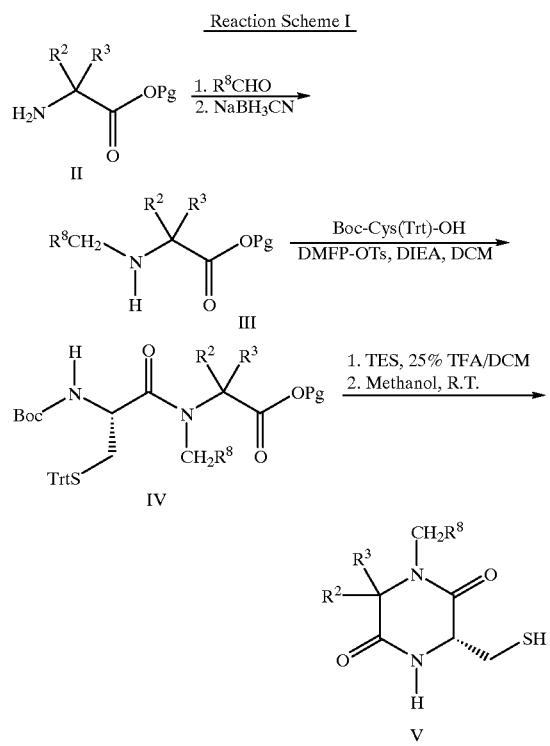

In one embodiment, reductive alkylation of an alpha amino acid of Formula II bearing an appropriate carboxyl protecting group yields a compound of Formula III, wherein $R^2$, $R^3$, and $R^8$ are as defined above. The reaction is preferably carried out in the presence of trimethylorthoformate and sodium cyanoborohydride. The amino acid Boc—Cys(Trt)—OH can optionally contain a single suitable substituent ($R^4$) on the amino group, e.g., an alkyl group, such that the resulting product V will contain a $R^4$ substituent replacing the hydrogen of the NH group.

The corresponding dipeptide can be produced by treatment of the N-alkylated amino acid of Formula III with an appropriately protected cysteine derivative. The reaction is preferably carried out in the presence of a coupling agent, for example DMFP.

Deprotection and cyclization affords the desired diketopiperazine V which is a compound of Formula I.

In another embodiment, the dipeptide is prepared by conducting reductive amination via coupling the aldehyde (i.e., $R^8CHO$) with an appropriately protected cysteine derivative followed by reaction of the amine with a protected suitable amino acid (i.e., $PgNCR^2R^3COOH$). Deprotection and cyclization affords the desired diketopiperazine of the formula I:

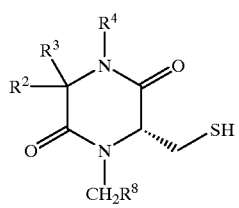

In either case, after deprotection, the terminal amino group can be alkylated prior to cyclization to provide for alkylated derivatives. Such alkylated groups include those recited above for the —$CH_2R^8$ derivatives.

The compounds of Formula II are either known amino acid derivatives or can be made from these derivatives by known methods. For example, the acid addition salt of compounds of Formula II can be treated with weak aqueous base (e.g., 5% aqueous sodium carbonate) to yield the corresponding free amine.

The intermediates of Formulas III and IV disclosed herein are in some forms novel compounds and form an aspect of the present invention as do the described processes for their preparation.

As mentioned above, the compounds of Formula I may exist in more than one diastereomeric form. Where the processes of the invention produce mixtures thereof, the individual isomers may be separated one from another by chromatography, e.g., HPLC.

Alternatively, separate diastereomeric compounds of Formula I can be obtained by using stereoisomerically pure starting materials or by separating desired isomers of intermediates at any stage in the overall synthetic process and converting these intermediates to compounds of Formula I.

The preparation of compounds of Formula I, wherein $R^1$ is —$CH_2R^8$ and $R^8$ is cyclohexy, $R^2$ is methylcyclohexyl, and $R^3$, $R^4$, $R^5$, and $R^6$ are hydrogen, from compounds of Formula VI is further illustrated in Reaction Scheme 2.

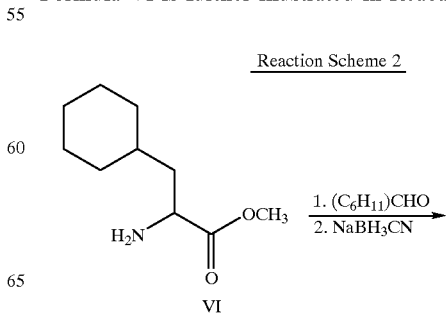

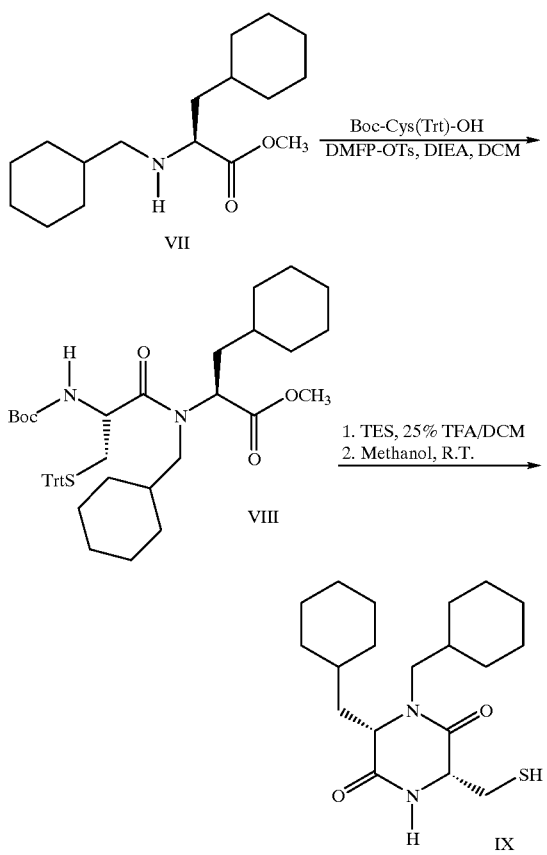

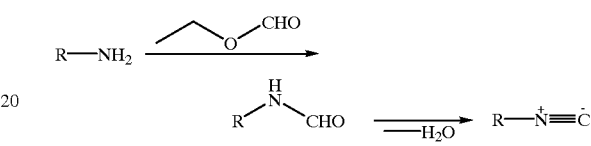

A single N-alkylated diketopiperazine of the present invention or a library of diketopiperazine derivatives also can be prepared under solid phase conditions, as described in copending applications: PCT patent application PCT/US95/07964; U.S. Ser. No. 08/265,578, filed Jun. 23, 1994; U.S. Ser. No. 08/393,318, filed Feb. 22, 1994; and U.S. Ser. No. 08/518,839, each of which is incorporated herein by reference for all purposes.

In the reaction schemes set forth above, the $R^1$ or $R^4$ substituent is necessarily —$CH_2R^8$ because the reaction proceeds from an imine which upon reduction, yields a methylene group adjacent to the nitrogen atom.

In another synthetic embodiment, diketopiperazines can be prepared via the known Ugi procedure, Ugi, et al. *Comprehensive Organic Synthesis for Synthetic Efficiency*, 20:1083 (1991). In this procedure, four components are combined, namely an amine (e.g., a first amino acid which can optionally be covalently linked to a solid support through the carboxyl group or having the carboxyl group protected), a carbonyl component (e.g., an aldehyde or ketone), an acid (e.g., a second amino acid having the amine group blocked or optionally can be covalently linked to a solid support) and an isocyanide.

Without being limited to any theory, it is believed that the reaction mechanism proceeds via formation of an imine from the amine component and the carbonyl component. The imine is then protonated by the acid to give the iminium ion. Nucleophilic attack of the isocyanide is followed by addition of the carboxylate component yielding an α-adduct that spontaneously rearranges into a stable α-acylaminocarboxamide. This rearrangement takes place only if a primary amine is employed. Secondary amines yield diacylamines which are acylating reagents and undergo further reactions depending upon the reaction conditions and nature of the other components. The reaction can be conducted either stepwise or in a single pot combining all four reagents. In the latter case, the one pot procedure is conducted without using any reagents but the four components described above.

Suitable amine components, carbonyl components and acid components are well known in the art. Likewise, isocyanides are either commercially available or can be prepared by conventional means well known in the art. For example, isocyanides can be prepared from primary amines by first forming the N-formyl amide therefrom and then dehydrating amide with thiophosgene in the presence of a tertiary amine (e.g., triethylamine) as shown in the reaction below:

Examples of commercially available isocyanides include, for instance, t-butyl isocyanide, 1,13,3-tetramethylbutyl isocyanide, tosylmethyl isocyanide, cyclohexyl isocyanide, benzyl isocyanide, methyl isocyanoacetate, ethyl isocyanoacetate, t-butyl isocyanoacetate, hexyl isocyanide, i-propyl isocyanide, 2,6-dimethylphenyl isocyanide, trimethylsilylmethyl isocyanide, diethyl(isocyanomethyl) phosphonate, 2-(4-morpholinyl)-ethyl isocyanide, 1,6-diisocyanohexane.

If the amine component is selected to be cysteine or a cysteine analogue, the $R^1$ is hydrogen and $R^4$ is —$CHR^8R^9$. Likewise, if the carboxyl component is selected to be cysteine or a cysteine analogue, the $R^1$ is —$CHR^8R^9$ and $R^4$ is hydrogen.

Assay Conditions

The assay for metalloprotease inhibition activity was performed using a HCBC buffer (pH 7.4, 20 mM Hepes (N-[2-hydroxyethyl]-piperazine-N'-[2-ethanesulfonic acid], 5 mM $CaCl_2$, 0.02% Brij35, 0.5 mM cysteine) which was vacuum degassed for 20 minutes prior to addition of the cysteine. Metalloprotease was added to the HCBC buffer at a concentration dependent upon the metalloprotease employed, i.e., 5 nM for collaganese-1, 5 nM for stromelysin-1, 0.5 nM for gelatinase-B, matrilysin and collagenase-3.

The compounds tested for metalloprotease inhibitor activity were first diluted into 50% methanol (first degassed by bubbling argon on ice for at least 30 minutes) in HCBC and always kept on ice.

The substrate, Mca, was obtained from Bachem Bioscience Inc. as product number M1895 and is a peptide substrate for metaloproteases having a fluorescent/quencher pair. In the intact peptide, the fluorescence is quenched by proximity of the quencher moiety to the fluorescence moiety. Upon digestion of this peptide by the metalloprotease, the quencher moiety is separated from the fluorescent moiety and, accordingly, metalloprotease activity can be determined by increases in fluorescence.

The substrate, 5 mM Mca in DMSO stock, was diluted into HCBC to 100 μM and then used in the assay as described below.

The assay was conducted by using multiple pipettes to add 172 μL of metalloprotease to each well and 8 μL of candidate inhibitor compound in 50% methanol. The solution was then mixed and maintained for 3 minutes. At that time, 200 μL of 100 μM of the Mca solution described above was added to initiate the reaction.

The degree of enzyme activity, as compared to the controls without inhibitor compound, was measured over a 30 minute period at 1 minute intervals by measuring the slope of the fluorescence curve via conventional methods.

The compounds 1–8 of Table I above are all active in inhibiting at least one of the tested metalloproteases in this assay and each of these compounds had an $IC_{50}$ of less than 100 μM for at least one such metalloprotease.

A metalloprotease assay is also described in U.S. patent application Ser. No. 08/549,346 filed Oct. 27, 1995 which application is incorporated herein by reference.

IV. Utility

A. Disease Indications

As previously stated, the compounds of the present invention have been found to be metalloprotease inhibitors. Metalloproteases are a family of zinc-containing peptidases as set forth in *Comprehensive Medicinal Chemistry: The Rational Design, Mechanistic Study & Therapeutic Application of Chemical Compounds*, Vol. 2, Pergamon Press, New York, 391–441 (1990), which is hereby incorporated by reference. Such proteases include, but are not limited to, metalloexoproteases, for example, angiotensin converting enzyme (ACE), aminoproteases, carboxyproteases, and renal proteases; metalloendopeptidases, for example, collagenase, endopeptidase 24.11, enkephalinase, and IgA proteinase; matrix metalloproteases; and tumor necrosis factor-α processing metalloproteases. As used herein, such metalloproteases do not include collagenase-1. Collagenase-1 refers to interstitial collagenase-1, matrix metalloproteinase-1, MMP-1, Type II collagenase-1), gelatinase (aka. type IV collagenase-1, matrix metalloproteinase-2, MMP-2, 72 kDa-gelatinase or type V collagenase-1, matrix metalloproteinase-9, MMP-9, 95 kDa-gelatinase) and stromelysin (aka. proteoglycanase, matrix metalloproteinase-3, MMP-3, procollagenase-1 activator, "transin"); leukocyte collagenase-1 and gelatinase; macrophage collagenase-1 and elastase; and tumor collagenase-1s. For a general review of the collagenase-1s and their role in normal and pathological connective tissue turnover, see *Collagenase-1 in Normal and Pathological Connective Tissues*, Woolley and Evanson, Eds., John Wiley & Sons, Ltd. (1988); *Comprehensive Medicinal Chemistry: The Rational Design, Mechanistic Study & Therapeutic Application of Chemical Compounds*, Vol. 2, Pergamon Press, New York, 391–441 (1990); and Docherty et al., "The Matrix Metalloproteinases and Their Natural Inhibitors: Prospects for Treating Degenerative Tissue Diseases," *Tibtech* 10: (1992).

Examples of metalloproteases include, by way of example, neutrophil collagenase; collagenase-3; gelatinase A; gelatinase B; stromelysins-2, and 3; matrilysin; macrophage elastase; membrane-type MMPs; agrrecanase, TNF-converting enzyme; other cytokine convertases; adhesion molecule "shedding enzymes"; endothelin converting enzyme; angiotensin converting enzyme; neutral endopeptidase; FTSH (a bacterial metalloprotease); metallo-lactamase (carbapenases); bacterial toxins (i.e., tetanus or botulism toxins), ras farnesyl protein transferase, and the like. See, for example, Hodgson, *Bio/Technology*, 13:554 (1995); Gordon, et al., *Clin. Exper. Rheum.*, 11(8):S91–S94 (1993); Ray, et al., *Eur. Respir. J.*, 7:2062–2072 (1994); O'Connor, et al., *Thorax*, 49: 602–609 (1994); Docherty, et al., *Tibtech*, Vol. 10, (1992); Newby, et al., *Basic Res. Cardiol.*, 89(Supp 1):59–70; Freije, et al., *J. Biol. Chem.*, 269(24):16766–16773 (1994); Shapiro, et al., *J. Biol. Chem.*, 268(32):23824–23829 (1993); Belaauoaj, et al., *J. Biol. Chem.*, 270(24):14568–14575 (1995); Gearing, et al., *Letters to Nature, Nature*, 370:555–557 (1994); McGeehan, et al., *Letters to Nature, Nature*, 370:558–561 (1994); Mohler, et al., *Letters to Nature, Nature*, 370:218–220 (1994); Sato, et al., *Letters to Nature, Nature*, 370:61–65 (1994); Crowe, et al., *J. Exp. Med.*, 181:1205–1210 (1995); Payne, *J. Med. Microbiol.*, 39:93–99 (1993); Deshpande, et al., *Toxicon*, 33(4):551–557 (1995); DePhillips, et al., *Eur. J. Biochem.*, 229:61–69 (1995).

ACE inhibitors, for example, have become an important class of drugs for controlling the most commonly encountered forms of hypertension and for controlling congestive heart failure.

Neutral endopeptidase is a membrane-bound zinc metalloendopeptidase located in the plasma membrane of many tissues. In mammalian brain the enzyme has been shown to be involved in the inactivation of the opiod peptides, methionine-enkephalin and leucine-enkephalin. Inhibitors of enkephalin degradation thus represent a new class of potential analgesic drugs.

Collagenases are zinc metallopeptidases that degrade triple helical collagen under physiological conditions. Inhibitors of collagenases are useful for elucidating the physiology of the associated enzymes and are useful for treating pathological conditions characterized by excessive proteolysis of collagen, such as occurs in rheumatoid arthritis, corneal ulceration and epidermolysis bullosa. The aminopeptidases, a multivariant group of zinc-containing exopeptidases that specifically cleave polypeptide changes at the amino terminus, are believed to play a role in the metabolism of many biologically active peptides.

The matrix metalloendoproteases include, but are not limited to stromelysins, collagenases, elastases, matrilysin and gelatinases, that are capable of degrading the major components of articular cartilage and basement membranes (Docherty et al., "The Matrix Metalloproteinases and Their Natural Inhibitors: Prospects For Treating Degenerative Tissue Diseases," *Tibtech* 10: (1992) with the understanding that said metalloproteases do not include stromelysin-1 and collagenase-1. More specifically, matrix metalloproteases include, without limitation, human skin fibroblast collagenase, human skin fibroblast gelatinase, purulent human sputum collagenases and gelatinase, and human stromelysin. These are zinc-containing metalloprotease enzymes, as are the angiotensin converting enzymes, the enkephalinases, and TNF.

Additional metalloproteases which may be or can be inhibited by the compounds of the present invention include tumor necrosis factor-α processing metalloprotease (TNF-α). TNF-α is a potent pro-inflammatory agent produced primarily by activated monocytes and macrophages. Recently, TNF-α convertase has been suggested to be a zinc-dependent endoproteinase, as reported in McGeehan et at., *Nature* 370:558–561 (1994); Gearing et al., *Nature* 370:555–557 (1994); and Mohler et al., *Nature* 370:218–220 (1994).

In addition to those enzymes specifically mentioned, as used herein, the term "matrix metalloprotease" will also include any zinc-containing enzyme that is capable of catalyzing the breakdown of structural proteins such as collagen, gelatin, elastase or proteoglycan under suitable assay conditions with the exception that the metalloproteases do not include collagenase-1 and stromelysin-1.

The range of therapeutic applications of the inhibitors described herein reflects the fundamental role of metalloproteases throughout the body, and extends to many diseases not primarily due to collagen and/or matrix destruction, but also involving tissue remodelling.

Specifically, the metalloprotease inhibitors of the present invention will provide useful treatments for arthritic diseases such as rheumatoid arthritis and osteoarthritis, septic arthritis, articular cartilage degradation, Reiter's syndrome, pseudogout, juvenile rheumatoid arthritis, scleroderma, soft tissue rheumatism, polychondritis and tendinitis; for bone resorption diseases such as osteoporosis, Paget's disease, hyperparathyroidism and cholesteatoma; for the recessive classes of dystrophic epidermolysis bullosa where the disease is linked to the overproduction of collagenase-1; for periodontal disease and related consequences of gingival collagenase production or of PMNL collagenase-1 production following cellular infiltration to inflamed gingiva; for ulceration including corneal, epidermal, or gastric ulceration and more specifically, for corneal ulceration induced by alkali or other burns, by radiation, by vitamin E deficiency or retinoid deficiency; for degenerative aortic disease associated with thinning of the medial aortic wall and thus, the prevention of events leading to acute and oftentimes fatal aortic aneurysms; for use as a birth control agent and for preventing ovulation; for glomerular disease (e.g., proteinuria), coronary thrombosis (e.g., atherosclerotic plaques), Crohn's disease, multiple sclerosis and the cachexia associated with cancer or human immunodeficiency virus infection; and, optionally in combination with current chemotherapy and/or radiation, for systemic chemotherapy of cancer, where collagenase-1 has been implicated in the neovascularization required to support tumor survival and growth, and in the penetration of tumor cells through the basement membrane of the vascular walls during metastasis.

As a particular example of the therapeutic value of metalloprotease inhibitors, chronic arthritic diseases lead to extensive loss of the collagen and proteoglycan components within the cartilage and bone of the affected joints. Neutral metalloproteases, especially collagenases and proteoglycanases, are currently thought to be the major enzymes involved. An imbalance between the levels of proteolytic enzymes and natural inhibitors will allow destruction of the connective tissue components to proceed. Restoration of the enzyme-inhibitor balance by treatment with synthetic inhibitors of metalloprotease thus offers a useful therapy for a wide range of connective tissue diseases in which collagenolytic activity is a causative or major contributory factor.

Also, the inhibitors are useful in the treatment of any disorder where excessive matrix loss is caused by metalloproteinase activity, and in the promotion of wound healing following surgery or other wound situations.

A limiting factor in the use of bone marrow transplantation for many advanced cancers with bone marrow involvement is the absence of adequate purging techniques. For example, metastatic interstitial pneumonitis following infusion of improperly purged bone marrow cells has been noted. The administration of the compounds of the present invention during infusion of unpurged bone marrow cells will alleviate the need for developing expensive purging techniques.

The compounds of this invention can also be labeled by association with a detectable marker substance (e.g., radiolabeled with $^{125}$I) to provide reagents useful in detection and quantification of metalloproteinase inhibitors in solid tissue and fluid samples such as blood or urine.

Appropriate assay conditions for the metalloprotease inhibition activity of the compounds of the present invention can be found, for example, in Knight et al., *FEBS Letters* 296(3):263–266(1992), and U.S. Pat. Nos. 4,743,587 and 5,240,958, which reference Cawston et al., *Anal. Biochem*, 99:340–345 (1979), Cawston et al., *Methods in Enzymology* 80:771 et seq. (1981); Cawston et al., *Biochem. J.*, 195:159–165 (1981) and Weingarten et al., *Biochem. Biophys. Res. Comm.*, 139:1184–1187 (1984), which references are hereby incorporated by reference. Any standard method for analyzing the breakdown of these structural proteins can, of course, be used. The matrix metalloprotease enzymes referred to in the herein invention are all zinc-containing proteases which are similar in structure to, for example, stromelysin or collagenase.

More specifically, the ability of candidate compounds to inhibit matrix metalloprotease activity can be tested in the assays described above. Isolated matrix metalloprotease enzymes can be used to confirm the inhibiting activity of the invention compounds, or crude extracts which contain the range of enzymes capable of tissue breakdown can be used.

B. Formulations

Also part of this invention is a pharmaceutical composition of matter comprising at least one compound of the invention described above, mixtures thereof, and/or pharmaceutical salts thereof; and a pharmaceutically-acceptable carrier therefore. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

Suitable carriers are well known in the art and vary with the desired form and mode of administration of the pharmaceutical composition. For example, they may include diluents or excipients such as fillers, binders, wetting agents, disintegrators, surface-active agents, lubricants and the like. Typically, the carrier may be a solid, liquid or vaporizable carrier, or combinations thereof. In one preferred embodiment, the composition is a therapeutic composition and the carrier is a pharmaceutically-acceptable carrier.

The compounds of the invention or salts thereof may be formulated together with the carrier into any desired unit dosage form. Typical unit dosage forms include tablets, pills, powders, solutions, suspensions, emulsions, granules, capsules, and suppositories.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous and intradermal) administration, with parenteral formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further comprise oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The compound of the invention may be present in the composition in a broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The invention also provides a method of treating or controlling disease states associated with metalloproteases (e.g., for inhibiting metalloproteases in patients afflicted with a disease state mediated by the metalloprotease) in a patient comprising administering to a patient an effective amount of the composition of this invention comprising any of the compounds of the present invention, pharmaceutically-acceptable salts thereof, or mixtures thereof.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. These include agents that are effective for the treatment of disease states involving tissue breakdown or inflammatory conditions in humans. Examples include any of those known in the art, such as known drugs for the treatment of arthritis, such as adrenocortical steroids, apazone, aspirin-like drugs, azathioprine, diclofenas, diflunisal, etodolac, fenamates, indomethacin, methotrexate, nabumetone, phenylbutazone, piroxicam, propionic acid derivatives, such as ibuprofen, naproxen, fenoprofen, ketoprofen, and flurbiprofen, salicylates, sulindac, and tolmetin; PMN elastase inhibitors such as those described in European Patent Application 337 549, glucagon, dextrose, diazoxide, phenytoin, thiazide diuretics and somatostatin, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained.

C. Mode of Administration

The mode of administration of the compounds of this invention depends on the disease to be treated and can be local administration (e.g., for ulceration or periodontal disease) or systemic administration (enteral or parenteral). The compound according to the invention, also referred to herein as the active ingredient, may be administered for therapy by any suitable routes, including oral, rectal, nasal, vaginal and parenteral (including intraperitoneal, subcutaneous, intramuscular, intravenous and intradermal) routes. For example, in the treatment of arthritis, the compounds can be administered orally, intravenously, subcutaneously or intramuscularly or, if appropriate, directly into the affected tissues by intraarticular injection. The compounds can be used in aqueous solution, or in the form of an ointment, gel or similar formulation for local applications or, if appropriate, in a pharmaceutical form which permits a slow release of the product, for example through encapsulation in an inert polymer.

It will be appreciated that the preferred route will vary with the condition and age of the patient, the nature of the disorder and the chosen active ingredient including other therapeutic agents. Preferred is the oral or intravenous route. However, other routes may also be utilized depending on the conditions of the patient and how long-lasting the treatment is.

The dosage of the compound of Formula I, pharmaceutically-acceptable salts or mixtures thereof, in the compositions of the invention administered to a patient will vary depending upon several factors, including, but not limited to, the age and weight of the patient, the type of disease state treated, how advanced the disease state is, the general health of the patient, the severity of the symptoms, whether the compound of Formula I is being administered alone or in combination with other therapies or other active ingredients, the incidence of side effects and the like.

In general, a dose suitable for application in the treatment of the above-mentioned conditions is about 0.001 to 100 mg/kg body weight/dose, preferably about 0.01 to 60 mg/kg body weight/dose, and still more preferably of about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered. The daily dose may be adjusted taking into account, for example, the above identified variety of parameters.

To achieve good plasma concentrations, the active compounds may be administered, for instance, by intravenous injection of an approximate 0.1 to 5% solution of the active ingredient, optionally in saline, or orally administered as a bolus.

In order to further illustrate the present invention and the advantages thereof, the following specific examples are given, it being understood that the same is intended only as illustrative and in nowise limitative.

In the examples below as well as elsewhere in this specification, all temperatures are in degrees Celcuis (° C.). Also, in the examples below as well as elsewhere in the specification, the following abbreviations are intended to have the meanings set forth below. If not defined, the abbreviation has its generally accepted meaning:

BOC=butyloxycarbonyl

Cha=cyclohexylalanine

DCM=dichloromethane

DIEA=diisopropylethylamine

DKP=diketopiperazine

DMF=dimethylformamide

DMFP-OTs=1,3-dimethyl-2-fluoropyridinium 4-toluenesulfonate eq.=equivalents
Fmoc=9-fluroenylmethoxycarbonyl
g=gram
HPLC=high performance liquid chromatography
mg=milligram
mL=milliliter
mmol=millimol
N=normal
TES=triethylsilane
TFA=trifluoroacetic acid
TMOF=trimethylorthoformate
Trt=trityl
μL=microliters

EXAMPLES

Example 1

Preparation of L-Cha-OMe

To a 0° C. solution of acetyl chloride (8 mL) in methanol (150 mL) was added L-cyclohexylalanine (L-Cha-OH, available from Novabiochem, 1 gram). The resulting solution was heated to reflux and stirred for 2 hours under argon. Concentration in vacuo yielded the desired hydrochloride salt as a white crystalline powder (1.20 g, 93%). The structure was confirmed by NMR.

The hydrochloride salt prepared above (529 mg) was dissolved in methylene chloride (150 mL). The solution was washed with 5% aqueous sodium bicarbonate (50 mL×2). The organic layer was dried over magnesium sulfate and concentrated to yield L-Cha-OMe as a colorless oil (364 mg, 82%).

Example 2

To a solution of L-Cha-OMe (364 mg, 1.96 mmol) in TMOF (15 mL) under argon was added cyclohexanecarboxaldehyde (1.12 mL, 9.82 mmol). After 15 minutes, a solution of $NaBH_3CN$ (308 mg, 4.9 mmol) in TMOF (15 mL) was added. The reaction mixture was stirred for one hour and was then cooled to 0° C. To the cold solution was added 2% aqueous hydrochloric acid (200 mL). The mixture was washed with petroleum ether (4×40 mL). Concentration aqueous sodium hydroxide was added dropwise to the aqueous layer at 0° C. until the pH was greater than 11. The product was extracted with ether (300 mL), washed with 5% aqueous sodium bicarbonate, and saturated aqueous sodium chloride and dried over magnesium sulfate. The organic layer was concentrated to an oil and diluted with petroleum ether. A 4N solution of hydrochloric acid in dioxane (2 mL) was added. Removal of the solvents followed by dilution with petroleum ether gave a white precipitate which was collected by filtration. The product (430 mg, 72%) was identified by NMR and mass spectroscopy.

Example 3

To a solution of Boc—Cys(Trt)—OH (584 mg, available from NovaBiochem) in methylene chloride (4 mL) was added DIEA (657 μL). To the clear solution was added DMFP-OTs (374 mg, 1.26 mmol, available from Fluka) and the reaction was stirred for 10 minutes. To the reaction mixture was then added the HCl salt of N-cyclohexylmethyl-L-Cha-Ome from Example 2 above. The resulting material was stirred at room temperature overnight, diluted with ether, washed with 2% aqueous hydrochloric acid (2×25 mL), 5% aqueous sodium bicarbonate (2×25 mL), and brine, and dried over magnesium sulfate. Concentration yielded crude product as an oil. Flash column chromatography on silica gel (eluting with ethyl acetate/hexane 1:9) gave the final product as a white foam (160 mg, 35%) which was identified by NMR and mass spectroscopy.

Example 4

To a mixture of the acylation product prepared above (60 mg) and TES (5 eq.) in dichloromethane (5 mL) under argon was added TFA (1.25 mL). The reaction was stirred for 20 minutes and the solvent was removed under vacuum. Degassed methanol (15 mL) was added and the reaction was stirred for 1 hour. The reaction was concentrated and purified by flash chromatography on silica gel (eluting with 2.5% methanol in dichloromethane) to yield the product as a white powder (20 mg, 65%).

The product was Ellman's reagent positive and was further identified by $^{13}C$ and $^1H$ NMR and by mass spectroscopy.

Example 5

Several different libraries of compounds of Formula I were prepared via combinatorial chemistry using solid phase synthesis wherein all compound variations of the different R groups described below have been prepared. The solid phase synthesis for each of these libraries is illustrated by the synthesis of (6S, 3R)-1,6-di(cyclohexylmethyl)-3-sulfanylmethyl-hexahydro-2,5-pyrazinedione on solid support.

Synthesis of (6S, 3R)-1,6-di(cyclohexylmethyl)-3-sulfanylmethyl-hexahydro-2,5-pyrazinedione.

A. Coupling Fmoc-Cha to TentaGel Resin

To a solution of Fmoc-cyclohexylalanine (2.4 g, 6.0 mmol) and DIEA (3.1 mL, 18 mmol) in DCM (15 mL) was added 1,3-dimethyl-2-fluoropyridium 4-toluenesulfonate (1.8 g, 6 mmol) under argon at room temperature. The solution was shaken for 10 minutes and TentaGel-S—OH resin (4.0 g, 1.2 mmol) added under argon. After mixing for 12 hours, the resin was filtered, washed with DMF, methanol, tetrahydrofuran and ether and then dried in vacuo. The loading of the resin was determined by Fmoc-cleavage with 20% piperidine/DMF. Yield was determined to be about 90%.

B. Reductive Alkylation with Cyclohexylcarboxaldehyde

To 200 mg (54 μmol) of $TGS-Cha-NH_2$ were added TMOF (2 mL) and cyclohexane carboxaldehyde (65 μL, 0.54 mmol). The resin was mixed for 30 minutes and acetic acid (31 μL, 0.54 mmol) was added. If that step was performed on the automated machine, the acetic acid would be added in 0.5 mL tetrahydrofuran. Mixing was continued for another 10 minutes and sodium cyanoborohydride in tetrahydrofuran (1.0 M solution, 1.5 mL) was added. After 30 minutes of mixing, the supernatant was drained and the resin washed with methanol, DMF and ether.

C. Coupling of Boc—Cys(Trt)—OH

A solution of Boc—Cys(Trt)—OH (339 mg, 1.25 mmol) and DIEA (653 μL, 3.75 mmol) in 1.5 mL anhydrous DMF was added to TGS-Cha-NH(Cha) followed by a solution of HATU (475 mg, 1.25 mmol) in 1.5 mL DMF. The resin was mixed for 12 hours. The supernatant was then drained and the resin washed three times with DMF followed by three ether washes.

D. Boc-deprotection and DKP-formation

For the Boc-deprotection, 2.5 mL of a 95% TFA/TES solution were added to the dry resin and mixed for 30 minutes. The TFA solution was drained and the resin washed three times with ether. A degassed solution of 1% acetic acid in toluene was added and mixed for 12 hours. The toluene solution was collected, concentrated and purified by HPLC if necessary. The DKP was characterized by NMR and mass spectroscopy.

The resulting libraries are defined in Tables II–V below. In the library of Table II, $R^1$, $R^3$, $R^5$, $R^6$ and $R^7$ are all hydrogen. In Tables III, IV and V, $R^3$, $R^4$, $R^5$, $R^6$ and $R^7$ are all hydrogen. In all libraries, n is one. All possible combinations of compounds were prepared.

TABLE II

| $R^4$ | $R^2$ |
|---|---|
| —$C_7H_{15}$ | —$CH_2$-p-ethoxy-φ |
| —$CH_2CH(CH_2CH_3)_2$ | —$(CH_2)_2$φ |
| —$CH_2$-p-ethyl-φ | —$CH_2$-cyclohexyl |
| —$CH_2CH(CH_3)_2$ | —$CH_2$-2-thienyl |
| —$(CH_2)_4CH_3$ | 4-Boc-2-histidinyl |
| —$CH_2$-cyclohexyl | 1-naphthyl |
| —$CH_2CH_2CH_3$ | 2-napthyl |
| —$CH_2CH_2CH(CH_3)_2$ | —$CH_2$φ |
| —$CH_2CH=CH$-φ (trans) | —$CH_2CH_2CH_3$ |
| —$CH_2CH(CH_3)CH_2CH_2CH=C(CH_3)_2$ | —$CH_2$-p-methoxy-φ |
| —$(CH_2)_2CH(CH_3)CH_2CH_2CH=C(CH_3)_2$ | —$CH(OBn)CH_3$ |
| —$(CH_2)_2CH(CH_3)$-φ | —$(CH_2)_4NHAc$ |
| —$CH_2CH=CHN(CH_3)_2$ (trans) | —$CH_2$-p-benzyloxy-φ |
| —$CH_2CH=CH(CH_2)_3CH_3$ (trans) | —$CH_2$-3-pyridyl |
| —$CH_2CH=CHCH=CHCH_2CH_3$ (trans, trans) | —$CH_2C(O)NH_2$ |
| —$CH_2CH=C(CH_3)_2$ | —$CH_2CH_2C(O)NH_2$ |
| —$CH_2CH=CH(CH_2)_2CH=CH$—$CH_2CH_3$ (trans, cis) | —$CH_2$—O—$CH_2$-φ |
| —$(CH_2)_9CH_3$ | —$CH_2CH_2CH_2CH_2$- (proline side chain) |

TABLE III

| $R^1$ | $R^2$ |
|---|---|
| —$(CH_2)_6CH_3$ | —$CH_2$-p-hydroxy-φ |
| —$CH_2CH(CH_2CH_3)_2$ | —$(CH_2)_2$φ |
| —$CH_2CH_2C(CH_3)_3$ | —$CH_2$-cyclohexyl (L) |
| —$(CH_2)_3SCH_3$ | —$CH_2$-2-thienyl (L) |
| —$CH_2$-p-φ-φ | —$CH_2CH(CH_3)_2$ |
| —$CH_2$—$CH(φ)_2$ | —$(CH_2)_3CH_3$ |
| —$CH_2CH_2CH_2$-φ | —$CH_2$-cyclohexyl |
| —$CH_2$-p-ethyl-φ | —$CH_2CH_2CH_3$ |
| —$CH_2CH(CH_3)_2$ | —$CH_2$-φ (L) |
| —$(CH_2)_4CH_3$ | —$CH_2$-φ (D) |
| —$CH_2C(CH_3)_3$ | —$CH_2$-p-methoxy-φ |
| —$CH_2$-cyclohexyl | —$CH_2$-S(Tr) |
| —$CH_2CH_2OCH_3$ | —$CH_2SCH_2$-p-methoxy-φ |
| —$CH_2$-p-methoxy-φ | —$CH_2CH_2$—S—$CH_3$ |
| —$CH_2$-p-N,N-dimethyl-φ | —$CH_2$-3-pyridyl |
| —$CH_2$-2-napththyl | —$CH_2$-thienyl (D) |
| —$CH_2CH_2CH_3$ | $CH_2CH_2$—C(O)NH(Tr) |
| —$(CH_2)_2CH(CH_3)_2$ | —$CH_2CH_2COO$-t-Bu |

TABLE IV

| $R^1$ | $R^2$ |
|---|---|
| —$(CH_2)_6CH_3$ | —$CH_2$-p-hydroxy-φ |
| —$CH_2CH(CH_2CH_3)_2$ | —$(CH_2)_2$φ |
| —$CH_2CH_2C(CH_3)_3$ | —$CH_2$-cyclohexyl (L) |
| —$(CH_2)_3SCH_3$ | $CH_2$-2-thienyl (L) |
| —$CH_2$-p-φ-φ | —$CH_2CH(CH_3)_2$ |

TABLE IV-continued

| $R^1$ | $R^2$ |
|---|---|
| —$(CH_2)_3$φ | —$(CH_2)_3CH_3$ |
| —$CH_2$-p-ethyl-φ | —$CH_2$-φ |
| —$CH_2CH(CH_3)_2$ | —$CH_2$-p-methoxy-φ |
| —$(CH_2)_4CH_3$ | —$CH_2$—S(Tr) |
| —$CH_2$-cyclohexyl | —$CH_2SCH_2$-p-methoxy-φ |
| —$CH_2CH_2OCH_3$ | —$CH_2CH_2$—S—$CH_3$ |
| —$CH_2$-p-methoxy-φ | —$CH_2$-3-pyridyl |
| —$CH_2$-p-N,N-dimethyl-φ | —$CH_2SCH_2NHC(O)CH_3$ |
| —$CH_2$-2-napththyl | —$(CH_2)_4NHC(O)$-3-pyridyl |
| —$(CH_2)_2CH(CH_3)CH_2CH_2CH=C(CH_3)_2$ | —$CH_2OCH_2$-φ |
| —$CH_2CH_2CH(CH_3)_2$ | —$CH_2CH_2OCH_2$-φ |
| —$CH_2CH=CH$-φ (trans) | $CH_2$-1-naphthyl |
| —$CH_2CH(CH_3)CH_2CH_2CH=C(CH_3)_2$ | —$CH_2$-3-indolyl |
|  | —$CH_2$-2,6-dichloro-4-hydroxy-φ |
|  | —$CH_2$-p-chloro-φ |
|  | —$CH_2$-2-pyridyl |
|  | —$(CH_2)_3NHC(=NH)NH_2$ |
|  | —$CH_2$-histidyl |
|  | —$(CH_2)_4NHC(O)CH_3$ |
|  | —$(CH_2)_2S(O)CH_3$ |
|  | —$(CH_2)_2S(O)_2CH_3$ |
|  | —$(CH_2)_4NH_2$ |
|  | —$CH_2$-p-nitro-φ |
|  | —$CH_2$-p-benzyloxy-φ |
|  | —$CH_2$-p-fluoro-φ |
|  | —$CH_2$-p-(φC(O))-φ |
|  | —$(CH_2)_2CH_3$ |
|  | —$CH_2OH$ |
|  | —$CH_2C\equiv CH$ |
|  | —$(CH_2)_5CH_3$ |

TABLE V

| $R^1$ | $R^2$ |
|---|---|
| —$(CH_2)_2CH_3$ | —$CH_2$-p-hydroxy-φ |
| —$CH_2CH=CHN(CH_3)_2$ (trans) | —$(CH_2)_2$φ |
| —$(CH_2)_8CH_3$ | —$CH_2$-cyclohexyl (L) |
| —$CH_2$-p-(4-pyrrolidyl)-φ | —$CH_2$-2-thienyl (L) |
| —$CH_2$-p-ethyoxy-φ | —$CH_2CH(CH_3)_2$ |
| —$CH_2$-(3-N,N-dimethylpropoxy)-φ | —$(CH_2)_3CH_3$ |
| —$CH_2$-p-(t-butoxy)-φ | —$CH_2$-φ |
| —$CH_2$-3-thiophenyl | —$CH_2$p-methoxy-φ |
| —$CH_2CH_2$—O—$CH_2CH_2$-φ | —$CH_2$—S(Tr) |
| —$CH_2$-p-benzyloxy-φ | —$CH_2SCH_2$-p-methoxy-φ |
| —$CH_2$-3-pyridyl | —$CH_2CH_2$—S—$CH_3$ |
| —$CH_2$-4-pyridyl | —$CH_2$-3-pyridyl |
| —$CH_2$-2-pyrrolyl | —$CH_2SCH_2NHC(O)CH_3$ |
| —$CH_2$-2-quinolinyl | —$(CH_2)_4NHC(O)$-3-pyridyl |
| —$CH_2CH=CH$-p-(N,N-dimethylamino)φ | —$CH_2OCH_2$-φ |
| —$CH_2$-p-(N,N-dimethylamino)φ | —$CH_2CH_2OCH_2$-φ |
| —$CH_2$-5-nitrothiophenyl | —$CH_2$-1-naphthyl |
| —$CH_2$-2-(n-methylpyrrolidinyl) | —$CH_2$-3-indolyl |
|  | —$CH_2$-2,6-dichloro-4-hydroxy-φ |
|  | —$CH_2$-p-chloro-φ |
|  | —$CH_2$-2-pyridyl |
|  | —$(CH_2)_3NHC(=NH)NH_2$ |
|  | —$CH_2$-histidyl |
|  | —$(CH_2)_4NHC(O)CH_3$ |
|  | —$(CH_2)_2S(O)CH_3$ |
|  | —$(CH_2)_2S(O)_2CH_3$ |
|  | —$(CH_2)_4NH_2$ |
|  | —$CH_2$-p-nitro-φ |
|  | —$CH_2$-p-benzyloxy-φ |
|  | —$CH_2$-p-fluoro-φ |
|  | —$CH_2$-p-(φC(O))-φ |
|  | —$(CH_2)_2CH_3$ |

TABLE V-continued

| R¹ | R² |
|---|---|
| | —CH₂OH |
| | —CH₂C≡CH |
| | —(CH₂)₅CH₃ |
| | —CH₂-2-(4-benyzl)-histidyl |

Example 6

Following the procedures set forth above, the following compounds have been prepared.

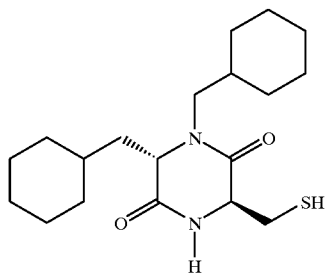

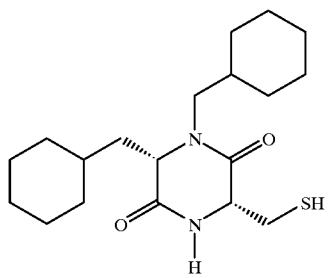

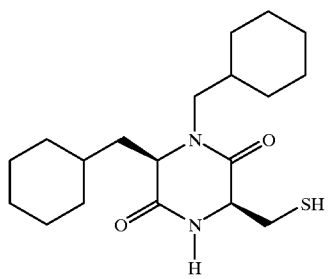

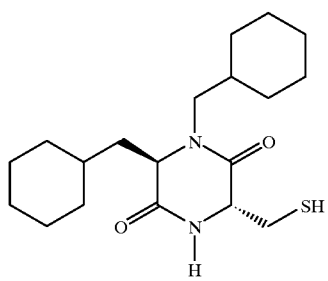

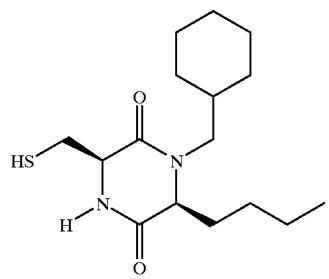

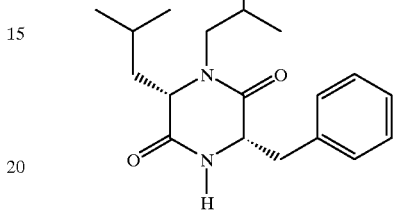

Example 7

This example illustrates the solid phase synthesis of diketopiperazine compounds using the Ugi reaction procedure well documented in the literature for the solution phase. Specifically, in this example, the following compound was prepared after decoupling from the resin.

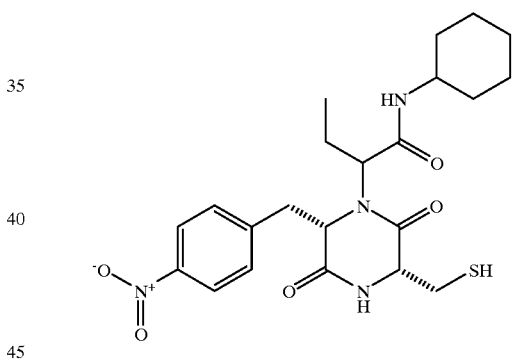

A. Coupling of FmocPhe(p-NO₂)OH to TentaGel Resin (TGS).

FmocPhe(p-NO₂)OH was coupled to TentaGel resin in the manner described above in Example 5A for FmocCha.

B. Solid Phase Ugi Reaction

To 200 mg (44 μmol) of TGS-Phe(p-NO₂)—NH₂ were added TMOF (1.5 mL) and propionaldehyde (32 μL, 0.44 mmol). The resin was mixed for about 20 minutes. A solution of BocCys(Trt)—OH (204 mg, 0.44 mmol) in methanol and cyclohexylisocyanide (56 μL, 0.44 mmol) were added. Mixing was continued for about 2 hours. The supernatant is then drained and the resin washed with DMF, ethanol and ether.

C. Boc-Deprotection and DKP-Formation.

For the Boc-deprotection, 2.5 mL of a 95% TFA/TES solution were added to the dry resin and mixed for 30 minutes. The TFA solution was drained and the resin washed three times with ether. A degassed solution of 1% acetic acid in toluene was added and mixed for about 12 hours. The toluene solution was collected, concentrated and purified by HPLC yielding 9 mg (44% overall) of a colorless crystalline material. The product was characterized by NMR and mass spectroscopy and confirmed as the compound described above.

Following the procedure set forth in this example, the following additional compound was prepared merely by substitution of the appropriate starting materials:

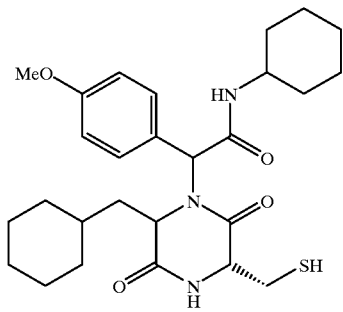

Both of the compounds described in Example 7 above have an $IC_{50}$ as described above of less than about 2 μM.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A compound of formula:

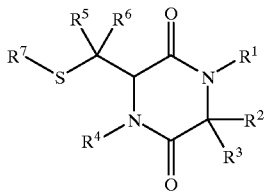

wherein
$R^1$ is —$CH_2R^8$; and
$R^8$ is selected from the group consisting of a cyclic, branched, or straight chain alkyl group of from 1 to 12 carbon atoms; an aryl group of from 6 to 10 carbon atoms; and arylalkyl of from 1 to 12 carbon atoms in the alkyl component thereof and 6 to 10 carbon atoms in the aryl component thereof;
$R^3$, $R^4$, $R^5$, $R^6$, and $R^7$ are hydrogen; and
$R^2$ is selected from the group consisting of a cyclic, branched or straight chain alkyl group of from 1 to 12 carbon atoms and arylalkyl;
or a pharmaceutical salt thereof.

2. The compound of claim 1, wherein $R^2$ is alkyl.

3. The compound of claim 1, wherein both $R^8$ and $R^2$ are alkyl.

4. The compound according to claim 1, wherein $R^2$ is arylalkyl.

5. The compound of claim 1, wherein $R^1$ is —$(CH_2)_p$-cyclohexyl and $R^2$ is —$(CH_2)_q$-cyclohexyl wherein p and q are independently integers from one to five.

* * * * *